United States Patent
Zussman et al.

(10) Patent No.: US 10,809,242 B2
(45) Date of Patent: Oct. 20, 2020

(54) METHOD FOR DETECTION OF AN ANALYTE/EXPLOSIVE ON A SAMPLE SURFACE

(71) Applicant: TECHNION RESEARCH & DEVELOPMENT FOUNDATION LTD., Haifa (IL)

(72) Inventors: Eyal Zussman, Haifa (IL); Yuval Eshed, Beit-Yehosahu (IL); Reshef Gal-Oz, Nesher (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 15/311,889

(22) PCT Filed: May 19, 2015

(86) PCT No.: PCT/IL2015/050531
§ 371 (c)(1),
(2) Date: Nov. 17, 2016

(87) PCT Pub. No.: WO2015/177792
PCT Pub. Date: Nov. 26, 2015

(65) Prior Publication Data
US 2017/0102372 A1      Apr. 13, 2017

(30) Foreign Application Priority Data
May 19, 2014     (IL) .......................................... 232696

(51) Int. Cl.
*G01N 33/22* (2006.01)
*D01D 5/00* (2006.01)
(Continued)

(52) U.S. Cl.
CPC ............. *G01N 33/227* (2013.01); *C09K 9/00* (2013.01); *D01D 5/0007* (2013.01); *D01D 5/34* (2013.01);
(Continued)

(58) Field of Classification Search
CPC ...................................................... G01N 33/22
(Continued)

(56) References Cited

U.S. PATENT DOCUMENTS 4,788,039 A * 11/1988 Glattstein .............. G01N 31/22
252/193
5,096,813 A * 3/1992 Krumhar .............. B65D 55/026
422/401
(Continued)

FOREIGN PATENT DOCUMENTS

WO     2009104176 A2     8/2009
WO     2014145745 A1     9/2014

OTHER PUBLICATIONS

Jouannet, D. et al, Polymer 1997, 38, 5137-5147.*
(Continued)

*Primary Examiner* — Arlen Soderquist
(74) *Attorney, Agent, or Firm* — The Roy Gross Law Firm, LLC; Roy Gross (57) ABSTRACT

Compositions comprising electrospun fibers and colorimetric detection encapsulated thereto are provided. Further, methods of use of said composition, including, but not limited to in-situ detection of molecules of interest, such as explosive compounds, are provided.

3 Claims, 5 Drawing Sheets

(51) Int. Cl.
    *D01D 5/34* (2006.01)
    *D01F 1/10* (2006.01)
    *C09K 9/00* (2006.01)
    *D01F 8/04* (2006.01)
    *G01N 21/78* (2006.01)

(52) U.S. Cl.
    CPC .............. *D01F 1/10* (2013.01); *D01F 8/04* (2013.01); *G01N 21/78* (2013.01); *G01N 33/22* (2013.01)

(58) Field of Classification Search
    USPC ........ 422/406, 420; 436/107, 110, 135, 164, 436/166, 169
    See application file for complete search history.

(56) References Cited

U.S. PATENT DOCUMENTS

| | | | | |
|---|---|---|---|---|
| 5,296,380 | A * | 3/1994 | Margalit | G01N 31/22 422/430 |
| 5,648,047 | A * | 7/1997 | Kardish | G01N 21/29 422/411 |
| 2002/0091011 | A1* | 7/2002 | Sosin | A63B 69/3623 473/278 |
| 2003/0044855 | A1* | 3/2003 | Anderson | B01J 19/0046 435/7.9 |
| 2004/0005360 | A1* | 1/2004 | Wang | A61K 9/2027 424/473 |
| 2005/0111805 | A1* | 5/2005 | Hertz | B82Y 20/00 385/125 |
| 2005/0214807 | A1* | 9/2005 | Johnson | C09B 11/08 435/6.12 |
| 2005/0287036 | A1* | 12/2005 | Eckels | B01L 3/5029 422/400 |
| 2006/0083657 | A1* | 4/2006 | McDonnell | A61L 2/28 422/504 |
| 2006/0121621 | A1* | 6/2006 | Bhandari | G01N 31/227 436/110 |
| 2006/0216833 | A1* | 9/2006 | Pagoria | B01L 3/5023 436/514 |
| 2007/0065944 | A1* | 3/2007 | Nunes | G01N 31/224 436/8 |
| 2007/0087198 | A1* | 4/2007 | Dry | B29C 73/22 428/408 |
| 2007/0111321 | A1* | 5/2007 | Deans | G01N 21/76 436/166 |
| 2007/0202009 | A1* | 8/2007 | Nunes | B01L 3/5023 422/400 |
| 2007/0264719 | A1* | 11/2007 | Santra | B82Y 15/00 436/57 |
| 2007/0286771 | A1* | 12/2007 | Nunes | B01L 3/5023 422/400 |
| 2008/0044909 | A1* | 2/2008 | Menzel | B82Y 30/00 436/56 |
| 2008/0170982 | A1* | 7/2008 | Zhang | B82Y 10/00 423/447.3 |
| 2009/0029480 | A1* | 1/2009 | Loane | G01N 21/78 436/170 |
| 2009/0233374 | A1* | 9/2009 | Zang | G01N 21/6428 436/106 |
| 2010/0129656 | A1* | 5/2010 | Zussman | A61L 31/10 428/376 |
| 2010/0178505 | A1* | 7/2010 | Rutledge | D01D 5/0007 428/394 |
| 2011/0081394 | A1* | 4/2011 | Zussman | B82Y 30/00 424/422 |
| 2011/0201242 | A1* | 8/2011 | Hur | C08L 31/04 442/181 |
| 2011/0259086 | A1* | 10/2011 | Harris | G01N 31/225 73/40.7 |
| 2012/0003746 | A1* | 1/2012 | Amisar | G01N 31/22 436/110 |
| 2012/0058166 | A1* | 3/2012 | Glenn, Jr. | D01F 1/10 424/401 |
| 2012/0189795 | A1* | 7/2012 | Wong | D01D 5/0069 428/36.91 |
| 2012/0193836 | A1* | 8/2012 | Sharma | D01D 5/0069 264/465 |
| 2012/0282705 | A1* | 11/2012 | Lei | G01N 21/643 436/110 |
| 2012/0292796 | A1* | 11/2012 | Peno | D01D 5/18 264/8 |
| 2013/0130398 | A1* | 5/2013 | Zang | G01N 21/78 436/128 |
| 2014/0065030 | A1* | 3/2014 | Genovese | G01N 31/22 422/402 |
| 2014/0080129 | A1* | 3/2014 | Klunder | C12Q 1/68 435/6.12 |
| 2014/0093969 | A1* | 4/2014 | Johnson | G01N 1/02 436/103 |
| 2014/0103583 | A1* | 4/2014 | Pham | D01D 5/0069 264/465 |
| 2014/0127824 | A1* | 5/2014 | Amisar | G01N 21/78 436/107 |
| 2014/0220704 | A1* | 8/2014 | Katz | G01N 33/227 436/501 |
| 2015/0004710 | A1* | 1/2015 | Gregory | G01N 33/227 436/75 |
| 2015/0056711 | A1* | 2/2015 | Lei | C08G 73/0206 436/98 |
| 2015/0072435 | A1* | 3/2015 | Hrboticka | G01N 21/78 436/135 |
| 2015/0118760 | A1* | 4/2015 | Zang | G01N 33/0057 436/110 |
| 2015/0268215 | A1* | 9/2015 | Tomellini | G01N 33/227 436/93 |
| 2015/0316483 | A1* | 11/2015 | Deans | G01N 21/76 506/12 |
| 2015/0330961 | A1* | 11/2015 | Verbeck, IV | G01N 1/44 436/98 |
| 2015/0360408 | A1* | 12/2015 | Menceloglu | D01D 5/0007 428/394 |
| 2016/0041135 | A1* | 2/2016 | Lannutti | G01N 21/6408 435/29 |
| 2016/0274030 | A1* | 9/2016 | Ruckh | G01N 21/6428 |

OTHER PUBLICATIONS

Nguyen, G. et al, Polymer International 2001, 50, 784-791.*
Wang, X. et al, Journal of Macromolecular Science, Part A Pure and Applied Chemistry 2002, 39,1241-1249.*
Wang, X. et al, Journal of Macromolecular Science, Part A Pure and Applied Chemistry 2002, 39,1251-1258.*
Wang, X. et al, Nano Letters 2002, 2, 1273-1275.*
Yu. J. H. et al, Advanced Materials 2004, 16, 1562-1566.*
Yoon, J. et al, Journal of the American Chemical Society 2007, 129, 3038-3039.*
Schantz, S. et al, Langmuir 2007, 23, 3590-3602.*
Naddo, T.et al, Journal of the American Chemical Society 2007, 129, 6978-6979.*
Kumar, A. et al, IEEE Conference on Technologies for Homeland Security 2008, 390-394.*
Yoon, J. et al, Advanced Functional Materials 2009, 19, 209-214.*
Long, Y. et al, Macromolecules 2009, 42, 6501-6509.*
Yang, Y. et al, Journal of Materials Chemistry 2009, 19, 7290-7295.*
Kuo, C.-C. et al, Macromolecular Rapis Communications 2010, 31, 65-70.*
Lv, Y.-Y. et al, Sensors and Actuators B 2010, 148, 233-239.*
Van der Schueren, L. et al, European Polymer Journal 2010, 46, 2229-2239.*
Lin, H. et al, Journal of the American Chemical Society 2010, 132, 15519-15521 with supporting information.*
Kacmaz, S. et al, Sensors and Actuators B 2011, 153, 205-213.*
Lee, J. et al, Journal of Materials Chemistry 2011, 21, 2648-2655.*
Wang, L.-Y. et al, Journal of Luminescence 2011, 131, 1277-1282.*

(56) References Cited

OTHER PUBLICATIONS

Poltue, T. et al, Materials Letters 2011, 65, 2231-2234.*
Yang, Y. et al, Journal of Materials Chemistry 2011, 21, 11895-11900.*
Wang, M. et al, Environmental Science & Technology 2012, 46, 367-373.*
Agarwal, A. et al, Sensors and Actuators B 2012, 161, 1097-1101.*
Wang, X. et al, Sensors and Actuators B 2012, 163, 186-193.*
Van der Schueren, L. et al, Dyes and Pigments 2012, 94, 443-451.*
Wang, Y. et al, Advanced Functional Materials 2012, 22, 3547-3555.*
Wang, W. et al, Chemical Communication 2012, 48, 6040-6042.*
Anzenbacher, P. et al, Chemistry A European Journal 2012, 18, 12712-12718.*
Niu, J. et al, Journal of Hazardous Materials 2013, 246-247, 119-125.*
Ongun, M. Z. et al, Sensors and Actuators B 2013, 181, 244-250.*
Ongun, M. Z. et al, Sensors and Actuators B 2013, 183, 11-19.*
Min, M. et al, Sensors and Actuators B 2013, 188, 360-366.*
Oter, O. et al, Sensor Letters 2013, 11, 1591-1599.*
Camposeo, a. et al, Nano Letters 2013, 13, 5056-5062.*
Syu, J.-H. et al, Advanced Functional Materials 2013, 23, 1566-1574.*
Lv, Y. et al, Sensors 2013, 13, 15758-15769.*
Kim, S.-H. et al, Fibers and Polymers 2013, 14, 1981-1984.*
Xue, R. et al, Sensors and Actuators B 2014, 192, 697-707.*
Ji, X. et al, Journal of Materials Chemistry B 2014, 2, 181-190.*
Thermal Transitions of Homopolymers: Glass Transition & Melting Point 2 pages, downloaded Oct. 31, 2017 from https://www.sigmaaldrich.com/content/dam/sigma-aldrich/docs/Aldrich/General_Information/thermal_transitions_of_homopolymers.pdf.*
Yoshimoto, H. et al, Biomaterials 2003, 24, 2077-2082.*
Tan, E. P. S. et al, Biomaterials 2005, 26, 1453-1456.*
Zussnnan, E. et al, Journal of Polymer Science: Part B: Polymer Physics 2006, 44, 1482-1489.*
Saeed, K. et al, Polymer 2006, 47, 8019-8025.*
Lee, S. J. et al, Biomaterials 2009, 29, 1422-1430.*
Marras, S. I. et al, Acta Biomaterialia 2008, 4, 756-765.*
Luo, X. et al, Macromolecules 2009, 42, 7251-7253.*
Zong, X. et al, Biomacromolecules 2003, 4, 416-423.*
Zhuo, H. et al, Journal of Applied Polymer Science 2008, 109, 406-411.*
Ding, W. et al, Macromolecular Materials and Engineering 2010, 295, 958-965.*
Scholten, E. et al, ACS Applied Materials & Interfaces 2011, 3, 3902-3909.*
Gu, X. et al, Polymer, 2012, 53, 5924-5934.*
Fouad, H. et al, International Journal of Electrochemical Science 2013, 8, 2293-2304.*
Wang, X.-D. et al, Angewandte Chemie International Edition 2008, 47, 7450-7453.*
Fang, Jian, Wang, Xungai and Lin, Tong 2011, Functional applications of electrospun nanofibers, in Nanofibers—production, properties and functional applications, InTech—Open Access Publisher, Rijeka, Croatia, pp. 287-326.
International Search Report for PCT/IL2015/050531 Completed Aug. 20, 2015; dated Sep. 3, 2015 3 Pages.
Written Opinion for PCT/IL2015/050531 Completed Aug. 20, 2015; dated Sep. 3, 2015 6 Pages.
Maria del Pilar Buera et al: "Glass Transition in Poly(vinylpyrolidone): Effect of Molecular Weight and Diluents", Biotechnology Progress, 1992, vol. 8, issue 2. pp. 144-148.
X. D. Huang et al: "Interpolymer Complexes through Hydrophobic Interactions: C60-End-Capped Poly(ethylene oxide)/Poly(methacrylic acid) Complexes", Macromolecules, 2000, vol. 33, pp. 8894-8897.
Shigeaki Morita: "Hydrogen-bonds structure in poly(2-hydroxyethyl methacrylate) studied by temperature-dependent infrared spectroscopy", Frontiers in Chemistry, Mar. 2014, vol. 2, article 10, pp. 1-5.

\* cited by examiner

Swab before detection    5 second after AN addition    After addition of one drop of water FIG. 10A     FIG. 10B     FIG 10C

METHOD FOR DETECTION OF AN ANALYTE/EXPLOSIVE ON A SAMPLE SURFACE

RELATED APPLICATIONS

This application is a national stage application under 371 of PCT/IL2015/050531 filed on May 19, 2015, and claims the benefit of IL patent application number 232696 filed on May 19, 2014. The disclosure of both applications are incorporated herein by reference in their entirety.

FIELD OF INVENTION

The present invention is directed to, inter alia, compositions comprising electrospun nanofibers and colorimetric reactants. The invention is further directed to methods of use of said compositions for detection of molecule of interest including but not limited to explosives.

BACKGROUND OF THE INVENTION

Recent security regulations and army operational requirements demand on-site detection of explosives to enable rapid identification so that swift action may be taken. Also, convenient methods for explosive residue collection and detection are desired for the analysis of pre-detonated devices or large pieces of post-blast debris, for which transport to an off-site laboratory is neither possible nor practical. The colorimetric field detection kits that are used by army and security forces around the world are based on reagents that dissolve in a liquid media and produce a colored compound when reacting with traces of explosives. However, liquid detection in a dynamic field environment is inconvenient, and potentially hazardous in case of spill and exposure to acidic solutions or fire. The majority of the dry detection methods that are used today rely on spectrometric techniques such as ion mobility spectrometry (IMS), analyzing either trace particles or vapor samples (J. Yinon and S. Zitrin, Modern Methods and Applications in Analysis of Explosives, Wiley, 1996). In IMS detection, a wipe taken from a contaminated surface in the field can be analyzed directly, eliminating sample preparation steps and thus increasing sample throughput. Although the instruments are sufficiently sensitive, operating it under field conditions is cumbersome.

An efficient method for fabrication of nanofibers is electrospinning. In this method, a liquid, typically a polymer solution is introduced into a strong electrostatic field, where the charged solution is drawn out into a jet. The jet then undergoes extensive stretching and thinning, with an extension rate on the order of $1000~s^{-1}$, and rapid evaporation of the solvent. Ultra-thin fibers, having diameters in the range of micrometers to tens of nanometers, are formed in milliseconds. The morphology of the electrospun fibers is governed by several parameters such as the applied voltage, needle-to-collector distance, feed rate of solution, temperature, humidity, as well as the properties of the polymer solution, such as electrical conductivity, surface tension, viscosity, viscoelasticity, solvent volatility and chemical compatibility between the polymer and the solvent. The high specific surface area of nanofibers is valuable for many applications, among them particle collection, filtration, sensors, wound dressing, tissue engineering and drug delivery.

Methods for manufacturing electrospun elements as well as encapsulating or attaching molecules thereto are disclosed, inter alia, in WO 2014/006621, WO 2013/172788, WO 2012/014205, WO 2009/150644, WO 2009/104176, WO 2009/104175, WO 2008/093341 and WO 2008/041183, to one of the present inventors and co-workers, the contents of which are fully incorporated herein by reference.

US Patent Application Publication No. 2012/0282705 provides explosives detection substrates which include an electrospun (electro)sprayed and/or dry spun aromatic polymer, such as polystyrene, and a small molecule fluorophore. Methods for detecting an explosive material are also provided relying on the amount of fluorescence emitted by the explosives detecting substrate.

US Patent Application Publication No. 2011/0086415 relates to pre-concentrator compositions, devices, systems, and/or methods for concentrating small quantities of chemical, biological, radioactive, nuclear and explosive agents (i.e., CBRNE compounds).

Recent publications reported tubular nanostructures for trace-level detection of explosives (Rui Li, et al. small 2012, 8, No. 2, 225-230; Ying Wang, et al. Adv. Funct. Mater. 2012, 22, 3547-3555; Shengyang Tao et al. J. Mater. Chem., 2007, 17, 2730-2736; Yufei Yang et al. J. Mater. Chem., 2011, 21, 11895-11900; Bowei Xu et al. Polym. Chem., 2013, 4, 5056; Yuan-Yuan Lv et al. Sensors and Actuators B 184, 2013, 205-211; Gudrun Bunte et al. Analytica Chimica Acta 591, 2007, 49-56; Yunxia Xu et al. Materials Letters 87, 2012, 20-23). The detection methods described in these publications rely on vapor diffusion of the targeted explosives and require fluorescence sensing such as by UV light for analysis.

There exists a long-felt need for highly sensitive and selective means of sampling contaminated surfaces and detecting molecules of interest, including but not limited to, explosive compounds, while maintaining safety of the user and the subject under observation. The development of inexpensive swabs capable of on-site detection of explosives, without the need of an additional detection device, is therefore desirable.

SUMMARY OF THE INVENTION

The present invention provides, in some embodiments, compositions and kits comprising electrospun nanofibers and colorimetric reactants encapsulated thereto. In some embodiments, the colorimetric reactants provide a colorimetric change in response to exposure to a molecule of interest, including but not limited to explosive compounds. The present invention further provides methods of preparation of said compositions and methods for the detection of molecules of interest by applying said compositions to a surface.

According to a first aspect, there is provided a composition comprising at least one type of electrospun nanofiber and at least one colorimetric reactant, the electrospun nanofiber comprises a shell and a core, said core comprises the at least one colorimetric reactant, and said shell has a glass transition between 70° C. to 150° C. In some embodiments, said shell is configured to break upon normal stress of 0.08-1 $kg/cm^2$ at a temperature range of −55° C. to 60° C.

In another embodiment, said composition has a porosity span from 60% to 95%. In another embodiment, said porosity comprises a plurality of interconnected tunnels within said composition. In another embodiment, the composition comprises pores having a pore size ranging from 0.1 to 100 micrometer.

In another embodiment, the composition comprises a shell having a thickness in the range of about 100 nm to about 5 micrometer. In another embodiment, the thickness of the shell is in the range of 0.1-1 micrometer. In another embodiment, the composition comprises a core having a diameter in the range of about 50 nm to about 10 micrometer.

In another embodiment, the electrospun shell of said nanofiber comprises a polymer selected from the group consisting of poly (methylmethacrylate-co-ethylacrylate) (PMCEA), poly (e-caprolactone) (PCL), fluoropolymer, tetrafluoroethylene, sulfonated tetrafluoroethylene, polyamide, poly(siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(carbonate), poly(acrylo nitrile), poly(ethylene oxide), polyaniline, polyvinyl carbazole, polystyrene, poly(vinyl phenol), polyhydroxyacid, poly(caprolactone), polyanhydride, polyhydroxyalkanoate, polyurethane, polysaccharide, or a combination thereof.

In another embodiment, the electrospun core of said nanofiber further comprises a polymer selected from the group consisting of, poly(acrylic acid), fluoropolymer, poly (vinyl acetate), polyacrylamide, poly(ethylene-co-vinyl acetate), poly(ethylene glycol), poly(methacrylic acid), polylactide polyglycolide, poly(lactide-coglycolide), polyanhydride, polyorthoester, poly(carbonate), poly(ethylene oxide), polyaniline, polyvinyl carbazole, polystyrene, poly (vinyl phenol), polyhydroxyacid, polysaccharide, or a combination thereof.

In another embodiment, the composition further comprises at least one polymer compound. In one embodiment, said at least one polymeric compound provides a support (e.g., mechanical support) to said composition. In another embodiment, said at least one polymer compound is selected from the group consisting of poly (e-caprolactone) (PCL), fluoropolymer, polyamide, poly(siloxane), poly(silicone), poly(ethylene), poly(vinyl pyrrolidone), poly(2-hydroxy ethylmethacrylate), poly(N-vinyl pyrrolidone), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(acrylo nitrile), poly(ethylene oxide), polyaniline, polyvinyl carbazole, poly(vinyl phenol), polyhydroxyacid, polyanhydride, polyhydroxyalkanoate, polyurethane, or a combination thereof.

In another embodiment, the composition comprises a plurality of electrospun nanofibers types and a plurality of colorimetric reactants, wherein each type of electrospun nanofiber comprises at least one type of a colorimetric reactant. In another embodiment, said composition is configured to enable a sequence of chemical reactions.

In another embodiment, said at least one colorimetric reactant has a pH value of at most 6. In another embodiment, said at least one colorimetric reactant has a pH value of at least 8. In another embodiment said at least one colorimetric reactant is reactive with at least one compound selected from a nitro-based compound, a peroxide-based compound, a chlorate and a bromated. In another embodiment, said at least one colorimetric reactant is an explosive detection reagent. In another embodiment, the explosive detection reagent is selected from the group consisting of: a Meisenheimer complex, a Griess reagent, a thymol reagent and a Nesslers reagent. In another embodiment, said composition is useful for detection of an explosive substance.

According to another aspect, there is provided method for the detection of a molecule of interest on a sample, the method comprising contacting (e.g., rubbing) the sample with the composition of the invention, wherein a colorimetric change within the composition indicates that the sample has at least trace amounts of the molecule of interest, thereby detecting a molecule of interest on said surface. In another embodiment, the molecule of interest is a hazardous substance. In another embodiment, the hazardous substance is an explosives substance. In another embodiment, said contacting is applying stress (e.g., normal stress) between said composition and said sample. In another embodiment, said stress is sufficient for breaking the electrospun shell. In another embodiment, said normal stress is of about 0.08-1 kg/cm$^2$. In another embodiment, said stress is sufficient for breaking the electrospun shell.

According to another aspect, there is provided kit for sampling and detecting a molecule of interest, the kit comprises at least one composition of the invention and optionally a carrier for said composition. In another embodiment, said carrier is selected from a glove and a stick. In another embodiment, said molecule of interest is a hazardous substance. In another embodiment, said hazardous substance is an explosive substance. In another embodiment, said kit is for sampling and detecting a plurality of molecules of interests, the kit comprises a plurality of compositions of the present invention, wherein each composition independently comprises at least one colorimetric reactant for detecting at least one molecules of interest.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2. The Greiss reaction for nitrate detection.

FIG. 7. Cryo high-resolution scanning electron microscopy (Cryo-HR-SEM) images of (7A) The cross-sections of reinforced core/shell fibers, made from DCHA core and 350 k PMCEA shell (core is in white color) and (7B) The core/shell-PAN matrix.

FIG. 8. Optical mages of (8A) Co-electrospun mat and (8B) after detection of 0.05 mg TNT. SEM images of DCHA as a core in 101K PMCEA shell fibers: (8C) Hollow fibers after breakage, presenting a brittle fracture, where the DCHA (the dark color) released and stained the substrate; (8D) PMCEA fracture pattern along the fiber, and (8E) DCHA which was not properly encapsulated by the PMCEA shell.

DETAILED DESCRIPTION OF THE INVENTION

The present invention provides compositions comprising electrospun fibers and methods of use thereof for the detection of molecules of interest. In some embodiments, the electrospun fibers comprise a shell and a core comprising colorimetric reactants. In some embodiments, the core of colorimetric reactants is encapsulated to the electrospun shell.

The present invention is based, in part, on detection of molecules of interest, including but not limited to an explosive substance, using wet chemistry analysis (i.e., chemistry performed substantially in the liquid phase). In another embodiment, the composition of the invention provides a reaction system in which at least one reaction is conducted in a solution. In another embodiment, the composition of the invention provides a reaction system in which a sequence of chemical reactions are conducted in a solution. As used herein, the term "a sequence of chemical reactions" refers to at least two, at least three, at least four or at least five chemical reactions. One skilled in the art will appreciate that the unique features of the composition of the invention (e.g., compartmentalization of reagents in separate microfibers) enables a reaction system in which a sequence of chemical reactions are conducted in a solution.

In another embodiment, the unique structure of the electrospun nanofibers described herein provides increased sampling and immediate detection of molecules of interest at the solid or liquid state. In another embodiment, detection of molecules of interest is achieved according to the invention when said molecule is in a liquid phase or a solid phase. In another embodiment, the composition and methods of the invention provide particulate detection of molecules of interest.

In another embodiment, the invention provides compositions and methods enabling a one-step analysis of a surface suspected of having trace amounts of a molecule of interest, such as, explosives. Without wishing to be bound by any theory or mechanism of action, the unique structure of the electrospun nanofibers comprising a shell and a core comprising or composed of colorimetric reactants encapsulated to the shell, wherein the shell is configured to break upon stress (e.g., by shear stress and/or by swiping a surface being analyzed) exposes the colorimetric reactants to the surface leading to the occurrence of a chemical reaction between the colorimetric reactants and molecules of interest upon the surface. In additional embodiments, the present invention provides a plurality of electrospun nanofiberes independently comprising colorimetric reactants, effective for performing a sequence of chemical reactions.

According to some embodiments, the invention provides compositions for sampling and detecting molecules of interest, such as explosive compounds, on surfaces for their subsequent immediate colorimetric detection.

Colorimetric detection methods are a low-cost tool for assessing the nature and extent of contamination and enabling on-site screening. The term "colorimetric" is defined as an analysis where the reagent or reagents of the composition of the invention produce a color change in the presence of an analyte, i.e., the molecule of interest.

In some embodiments, the composition of the invention may be in the form of a device, e.g., a swab. In some embodiments, the swab provides sampling and detection in a single medium. In some embodiments, the swab provides means for holding, protecting, and/or maintaining fibers of the invention in a non-broken (whole) form. In some embodiments, the swab's structure provides a multi-scale assembly of nano scale fibers, micro scale fibers, or a combination thereof. In another embodiment, the multi-scale assembly of the fibers within a swab creates an increased surface area. In some embodiments, the increased surface area of the swab enables enhanced collection efficiency of molecules of interest.

The device described herein, e.g., in a form of a swab, can be in different sizes depending on the type of surface to be sampled. The shape of the swab can be, without limitation, circular, oval, square, rectangular, or any other shape suitable to purpose of the swab. In another embodiment, the swab is affixed to the end of a glove or a holder. The swab can be permanently or temporarily affixed to the glove or holder for ease of manipulation, usage and sampling. In another embodiment, the swab is disposable. The swab may be used by military, law enforcement, homeland security, and others.

In another aspect, the present invention provides a gel encapsulated swab. In some embodiments, said gel encapsulated swab comprises at least two layers of electrospun fibers and a detecting paste (i.e., a layer comprising colorimetric reagent) between the at least two layers of electrospun fibers.

Explosives

In particular embodiments, the present invention provides compositions and methods for detection of explosives molecules. In another embodiment, the colorimetric reactants encapsulated or attached to the electrospun core are explosive-detection reagents.

As exemplified herein below, the compositions of the invention were highly effective in sampling and detecting of 2,4,6-trinitrotoluene (TNT) and ammonium nitrate, using the TNT-DCHA charge transfer complex formation, or the Greiss three-step reaction, respectively. An additional composition was effective in sampling and detecting potassium chlorate, using NPA oxidation.

In another embodiment, the compositions and methods of the invention are useful for detection of settled explosive compounds. In another embodiment, the compositions and methods of the invention are useful for detection of solid or liquid explosive compounds.

In some embodiments, the present invention provides a highly sensitive detection composition. Accordingly, in some embodiments, the composition described herein is capable of detecting an explosive material in very small amounts. Sensitivity may be measured by the amount (in weight) of explosive material required to produce a colorimetric reaction with the reagents within the electrospun fiber. In some embodiments, the composition is capable of producing a colorimetric reaction in the presence of an explosive material in an amount less than about 10 less than about 1 µg, less than about 500 ng, less than about 250 ng or less than about 100 ng. Each possibility represents a separate embodiment of the present invention.

The term "explosives", as used herein is intended to encompass explosive compounds, explosive byproducts as well as explosive precursors. According to some embodiments, the explosives are selected from nitroaromatics, organic nitrates (also termed "nitroesters"), nitramines, inorganic nitrates, chlorates and bromates. Examples of explosive agents that may be detected by the methods and compositions described herein include but are not limited to, ammonium nitrate/fuel oil (AN/FO), amatol, ammonium nitrate, ammonium picrate, dynamite, guanidine nitrate, gunpowder, octahydro-1,3,5,7-tetranitro-1,3,5,7-tetrazocine (HMX), hexanitrostilbene, lead azide, lead styphnate, mannitol hexanitrate, mercury fulminate, naphthacene, nitroguanidine, pentaerythritol tetranitrate (PETN), picric acid, hexahydro-1,3,5-trinitro-1,3,5-triazine (RDX), 1,3,5-trinitrobenzene (TNB), 1,3-dinitrobenzene (DNB), methyl-2,4,6-trinitrophenylnitramine (Tetryl), nitrobenzene (NB), 2,4,6-trinitrotoluene (TNT), picric acid (PA), 2,4-dinitrotoluene (24DNT), 2,6-dinitrotoluene (26DNT), o-nitrotoluene (2NT), m-nitrotoluene (3NT), p-nitrotoluene (4NT), nitroglycerin (NG), 4-amino-2,6-dinitrotoluene (4-Am-DNT), 2-amino-4,6-dinitrotoluene (2-Am-DNT), pentaerythritol tetranitrate (PETN), 2,3-dimethyl-2,3-dinitrobutane (DMNB), acetone peroxide (TATP), triaminotrinitrobenzene (TATB) and tritonal. Each possibility represents a separate embodiment of the present invention.

In another embodiment, the colorimetric reactants are reactive with nitroaromatics, including but not limited to TNT, DNT and tetryl. In another embodiment, the colorimetric reactants are reactive with nitramines or nitrate esters including but not limited to RDX, HMX, PETN, EGDN and NG. In another embodiment, the colorimetric reactants are reactive with inorganic nitrates including but not limited to urea nitrate, ammonium nitrate and black powder. In another embodiment, the colorimetric reactants are reactive with chlorate and/or bromates including but not limited to potassium chlorate and potassium bromated. In another embodiment, the colorimetric reactants are reactive with peroxides e.g. TATP and HMTD. In another embodiment, the colorimetric reactants are reactive with acids e.g. nitric acid, sulfuric acid and citric acid. In another embodiment, the colorimetric reactants are reactive with bases e.g. potassium hydroxide and sodium hydroxide TNT Colorimetric Detection:

TNT colorimetric detection typically relies on the Meisenheimer reaction (J. Meisenheimer, "Ueber Reactionen aromatischer Nitrokörper," Justus Liebigs Ann. Chem. 323 (2), 205 (1902)) to create a chromophore from the nitroaromatic explosive molecule and a hydroxyl ion (OH—). In some embodiments, a Meisenheimer Complex solution is used as a colorimetric reactant of the invention. Typically, tetrabutylammonium hydroxide in ethanol gives a color indication for TNT, tetryl, and trinitrobenzene.

According to another embodiment, the colorimetric detection is based on cymantrene (cyclopentadienyl manganesetricarbonyl), which exhibits a color change when it comes into contact with several nitroaromatics, under UV radiation (S. J. Toal and W. C. Trogler, J. Mater. Chem. 16, 2871, 2006; L. M. Dorozhkin, et al., Sensors and Actuators B 99, 568, 2004).

In another embodiment, a dicyclohexylamine (DCHA) based colorimetric reactant is used. DCHA based colorimetric detector is known in the art for detection of TNT and Tetryl (2,4,6-trinitrophenyl-N-methylnitramine) (A. Uzer, et al. 2004, Anal. Chim. Acta 505, 83; A. Uzer, et al. 2009, Talanta 78, 772). Its detection is based on intermolecular charge-transfer (CT) between the electron-attracting nitroaromatics and electron-donating amine, DCHA (FIG. 1), resulting in a deep violet color and UV-Vis absorbance. The CT between primary amines and explosives was may also be used for the detection of explosive species, using nanowire sensor arrays without any further chemical treatment (Y. Engel, 2010, et al. Angew. Chem. Int. Ed. 49, 6830).

Nitrate Colorimetric Detection:

In some embodiments, a Griess reaction is used for colorimetric detection of nitrate. The Griess three-step reaction is known in the art as the standard nitrate colorimetric detection method (J. P. Griess, Philos. Trans. R. SOC. London, 164, 683, 1864) as presented in FIG. 2. In this reaction, the nitrate is first reduced to nitrite, which then reacts to conjugate a sulfanilic acid to an aromatic amine and produces an azo dye product, having a deep violet color and a 540 nm visible light absorbance.

Figure 3:
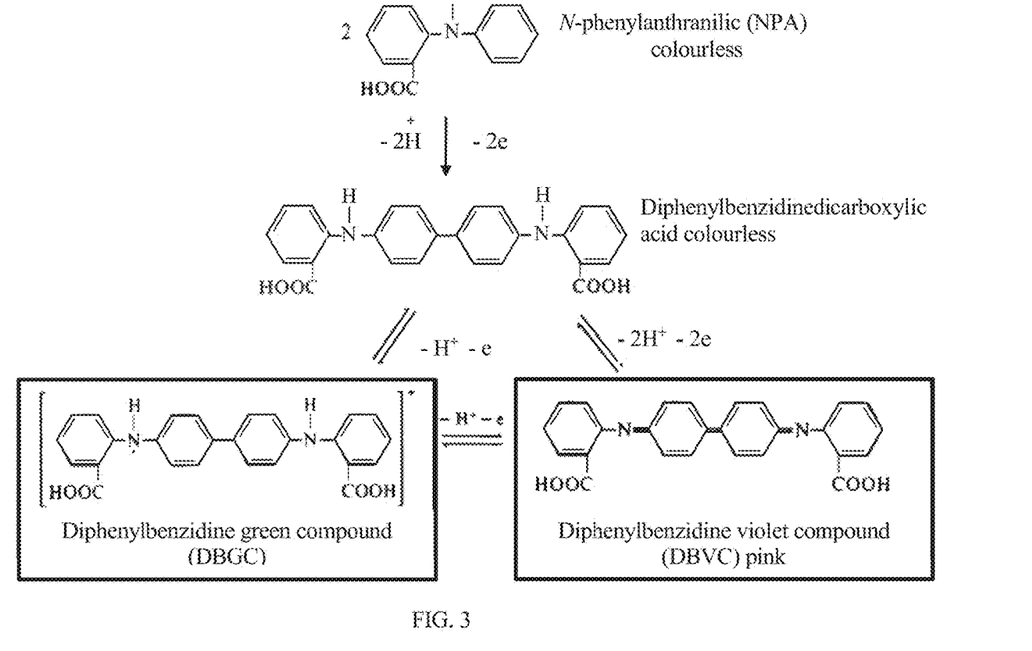
FIG. 3: The oxidation mechanism of N-phenylanthranilic acid (NPA).
Figure 4:
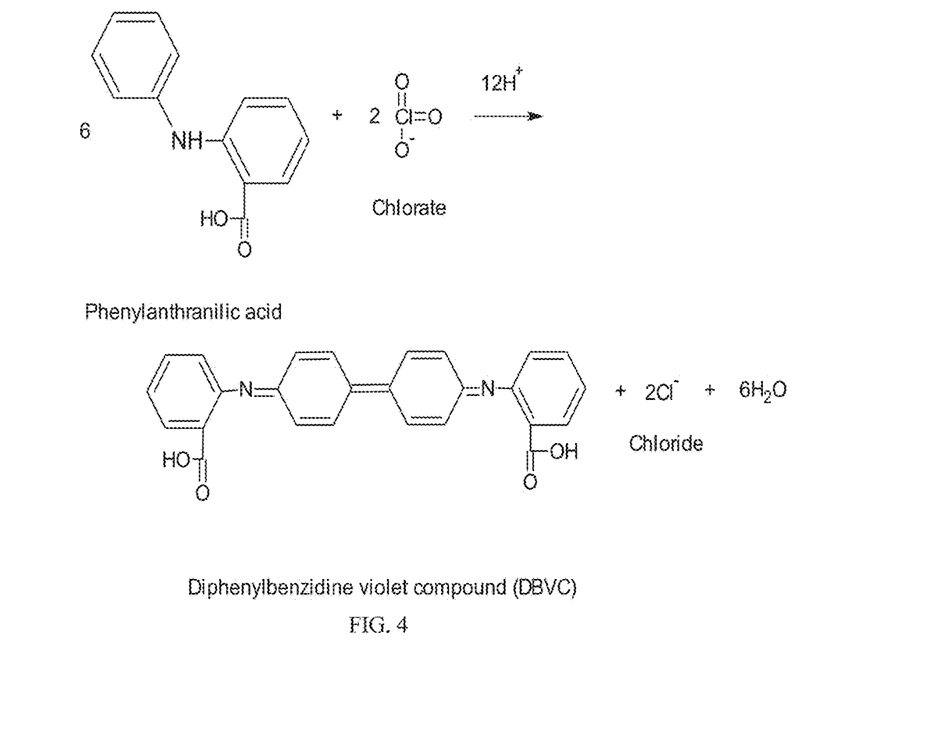
FIG. 4: The chlorate colorimetric detection.

Chlorate Colorimetric Detection:

In some embodiments, N-phenylanthranilic acid (NPA) is used for colorimetric detection of chlorates. As known in the art NPA oxidation results in two detection colored products: (1) green ($\lambda$max=430 nm) and (2) violet ($\lambda$max=550 nm); depending on the oxidant's nature, as presented in FIG. 3, (K. Sriramam, Talanta, 20, 383, 1973). In the presence of NPA (FIG. 4), the colorimetric reaction for chlorates is immediate, giving a deep violet colored product; whereas the colorimetric reaction of other strong oxidizers is delayed, resulting in a pale colored product compared to chlorate.

In some embodiments, the methods of the present teachings allow for the detection of explosive materials on surfaces such as hands, clothing, cars, packages, luggage, door handles, buildings, land, desks, computers, and more.

In another embodiment, the at least one colorimetric reactant of the composition of the invention has a pH value of at most 6. In another embodiment, said at least one colorimetric reactant has a pH value of at least 8. In another embodiment said at least one colorimetric reactant is reactive with at least one compound selected from a nitro-based compound, a peroxide-based compound, a chlorate and a bromated. In another embodiment, said at least one colorimetric reactant is an explosive detection reagent. In another embodiment, the explosive detection reagent is selected from the group consisting of: a Meisenheimer complex, a Griess reagent, a thymol reagent and a Nesslers reagent. In another embodiment, said composition is useful for detection of an explosive substance.

In some embodiments, molecules that may be detected by the methods and compositions of the disclosure include toxic or chemical agents, and pollutants, such as but not limited to, Tabun, Sarin, Soman, VX, mustard, lewisite, phosgene, chlorine, ammonia, cyanide, Mace®, pepper spray, nerve agents, vesicants, industrial chemicals, and riot control agents.

Electrospun Fibers

According to some embodiments, the compositions of the invention comprise at least one type of electrospun nanofiber and at least one colorimetric reactant encapsulated therein. In some embodiments, the electrospun nanofiber comprises a shell and a core, wherein the core comprises or is composed of the at least one colorimetric reactant.

According to another embodiment, the fibers of the invention are not hollow or of a tubular shape, but are composed of a brittle (or fragile) shell and a core of colorimetric reactant(s). In another embodiment, the shell is substantially filled with the colorimetric core. As used herein, a brittle shell refers to a shell configured to break upon stress, thereby exposing (or releasing) the core's colorimetric reactants.

In another embodiment, the shell has a glass transition of at least 50° C., at least 55° C., at least 60° C., at least 65° C., at least 70° C., at least 75° C., or at least 80° C. In another embodiment, the shell has a glass transition of at least 70° C. In another embodiment, the shell has a glass transition of at most 150° C., at most 145° C., at most 140° C., at most 135° C., at most 130° C., at most 125° C., or at most 120° C. In another embodiment, the shell has a glass transition of at most 150° C.

"Tg" or "glass transition temperature" of a polymer is the temperature at which a polymer transitions from a rigid, glassy state at temperatures below its Tg to a fluid or rubbery state at temperatures above Tg. The Tg of a polymer is measured by differential scanning calorimetry (DSC) using the mid-point in the heat flow versus temperature transition as the Tg value.

As used herein, the term "configured to break upon stress" included but is not limited to normal stress, shear stress, or a combination of normal stress and shear stress, as such as developed upon swiping a surface being analyzed. In some embodiments, said shell is configured to break upon normal stress of at least 0.08, at least 0.09, at least 0.1, at least 0.15, at least 0.2, at least 0.25, at least 0.3, at least 0.35, at least 0.4, at least 0.45 or at least 0.5 kg/cm$^2$ at a temperature range of −55° C. to 60° C. In some embodiments, said shell is configured to break upon normal stress of at most 0.6, at most 0.65, at most 0.7, at most 0.75, at most 0.8, at most 0.85, at most 0.9, at most 0.95 or at most 1 kg/cm$^2$ at a temperature range of −55° C. to 60° C. "Normal stress" is defined herein as the stress acting perpendicular to a surface.

In some embodiments, the core is a liquid core. In another embodiment, the shell is i.e., is at a state of liquid. In another embodiment, said shell has a low porosity and diffusion for preventing leakage of the core (e.g., a liquid core) encapsulated within the shell. In some embodiments, said shell has a low porosity and diffusion in the order of about $10^{-10}$ (cm$^2$ s$^{-1}$), or any other order as determined by a skilled artisan, according to the core's state.

In another embodiment, said composition has a porosity span of at least 30%, at least 35%, at least 40%, at least 45%, at least 50%, at least 55%, at least 60%, at least 65%, at least 70%, at least 75%, at least 80%, at least 85%, at least 90% or at least 95%. In another embodiment, said porosity comprises a plurality of interconnected tunnels within said composition. In another embodiment, the composition comprises pores having a pore size ranging from 0.1 to 100 micrometer.

In another embodiment, the composition comprises a plurality of electrospun nanofibers types and plurality colorimetric reactants, wherein each type of electrospun nanofiber comprises at least one type of a colorimetric reactant. In another embodiment, said composition is configured to enable a sequence of chemical reactions.

The term "electrospun" or "(electro)sprayed" when used in reference to polymers are recognized by persons of ordinary skill in the art and includes fibers produced by the respective processes. Such processes are described in more detail infra.

Methods for manufacturing electrospun elements as well as encapsulating or attaching molecules thereto are disclosed, inter alia, in WO 2014/006621, WO 2013/172788, WO 2012/014205, WO 2009/150644, WO 2009/104176, WO 2009/104175, WO 2008/093341 and WO 2008/041183, all to one of the present inventors and co-workers, the contents of which are fully incorporated herein by reference.

Manufacturing of electrospun elements can be done by an electrospinning process which is well known in the art. Following is a non-limiting description of an electrospinning process. One or more liquefied polymers (i.e., a polymer in a liquid form such as a melted or dissolved polymer) are dispensed from a dispenser within an electrostatic field in a direction of a rotating collector. The dispenser can be, for example, a syringe with a metal needle or a bath provided with one or more capillary apertures from which the liquefied polymer(s) can be extruded, e.g., under the action of hydrostatic pressure, mechanical pressure, air pressure and high voltage.

The rotating collector (e.g., a drum) serves for collecting the electrospun element thereupon. Typically, but not obligatorily, the collector has a cylindrical shape. The dispenser (e.g., a syringe with metalic needle) is typically connected to a source of high voltage, preferably of positive polarity, while the collector is grounded, thus forming an electrostatic field between the dispenser and the collector. Alternatively, the dispenser can be grounded while the collector is connected to a source of high voltage, preferably with negative polarity. As will be appreciated by one ordinarily skilled in the art, any of the above configurations establishes motion of positively charged jet from the dispenser to the collector. Inverse electrostatic configurations for establishing motions of negatively charged jet from the dispenser to the collector are also contemplated.

At a critical voltage, the charge repulsion begins to overcome the surface tension of the liquid drop. The charged jets depart from the dispenser and travel within the electrostatic field towards the collector. Moving with high velocity in the inter-electrode space, the jet stretches and solvent therein evaporates, thus forming fibers which are collected on the collector, thus forming the electrospun element.

As used herein, the phrase "electrospun element" refers to an element of any shape including, without limitation, a planar shape and a tubular shape, made of one or more non-woven polymer fiber(s), produced by a process of electrospinning. When the electrospun element is made of a single fiber, the fiber is folded thereupon, hence can be viewed as a plurality of connected fibers. It is to be understood that a more detailed reference to a plurality of fibers is not intended to limit the scope of the present invention to such particular case. Thus, unless otherwise defined, any reference herein to a "plurality of fibers" applies also to a single fiber and vice versa. In some embodiments, the electrospun element is an electrospun fiber, such as electrospun nanofiber. As used herein the phrase "electrospun fiber" relates to a fibers formed by the process of electro spinning.

The electrospun fibers of the invention comprise an electrospun shell and a core. As used herein, the phrase "electrospun shell" refers to an element of a tubular shape, made of one or more polymers, produced by the process of electrospinning. As used herein the phrase "core" refers to an internal layer within the electrospun shell, which is made of at least one colorimetric reactant, and optionally one or more polymers. In another embodiment, the core is encapsulated within the electrospun shell. In some embodiments, the core is an electrospun core, i.e., prepared by the process of electrospinning. In some embodiments, the fiber's core is not in a solid state. In some embodiments, the fiber's core is in a liquid state. In some embodiments wherein the fiber's core is in a liquid state, said shell has low porosity, as such as to prevent diffusion or leakage of the liquid core.

One of ordinary skill in the art will know how to distinguish an electrospun object from objects made by means which do not comprise electrospinning by the high orientation of the macromolecules, the shell morphology, and the typical dimensions of the fibers which are unique to electrospinning.

According to some embodiments of the invention the thickness of the electrospun shell of the invention can vary from a few nanometers to several micrometers, such as from about 100 nm to about 20 μm (micrometer), e.g., from about 200 nm to about 10 μm, from about 100 nm to about 5 μm, from about 100 nm to about 1 μm, e.g., about 500 nm. In another embodiment, the composition comprises a core having a diameter in the range of about 50 nm to about 10 micrometer.

According to some embodiments of the invention, the electrospun fiber may have a length which is from about 0.1 millimeter (mm) to about 20 centimeter (cm), e.g., from about 1-20 cm, e.g., from about 1-10 cm. According to some embodiments of the invention, the length (L) of the electrospun fibers of some embodiments of the invention can be several orders of magnitude higher (e.g., 10 times, 100 times, 1000 times, 10,000 times, e.g., 50,000 times) than the fiber's diameter (D).

According to some embodiments of the invention, the electrospun fiber is produced by a method which comprises co-electrospinning two solutions through co-axial capillaries, wherein a first solution of the two solutions is for forming a shell of the fiber and a second solution of the two solutions is for forming a core within the shell. In some embodiments, said solution is a polymeric solution.

As used herein the phrase "co-electrospinning" refers to a process in which at least two solutions are electrospun from co-axial capillaries (i.e., at least two capillary dispensers wherein one capillary is placed within the other capillary while sharing a co-axial orientation) forming the spinneret within an electrostatic field in a direction of a collector. The capillary can be, for example, a syringe with a metal needle or a bath provided with one or more capillary apertures from which the solution can be extruded, e.g., under the action of hydrostatic pressure, mechanical pressure, air pressure and/or high voltage.

For forming a core/shell structure by electro spinning, a first solution is injected into the outer capillary of the co-axial capillaries while a second solution (also referred herein as a core solution) is injected into the inner capillary of the co-axial capillaries. In some embodiments wherein the core is not a liquid core, the first solution (which is for forming the shell/sheath of the fiber) solidifies faster than the core solution. In some embodiments, the formation of core/shell structure also requires that the solvent of the core solution be incapable of dissolving the first solution. The solidification rates of the first and second solutions are critical for forming a core/shell fiber. As a non-limiting example of a core/shell fiber of about 100 μm wherein the core is not a liquid core, the solidification of the first solution can be within about 30 milliseconds (ms) while the solidification of the core polymer, if occurs, can be within about 10-20 seconds. The solidification may be a result of polymerization rate and/or evaporation rate.

According to some embodiments of the invention, the solvent of the polymeric solution evaporates faster than the solvent of second solution (e.g., the solvent of the first solution exhibits a higher vapor pressure than the solvent of the second solution). In one embodiment, the shell solidifies and the core remains in a liquid form. In one embodiment, the shell solidifies faster than the core.

The flow rates of the first and second solutions can determine the fibers outer and inner diameter and thickness of shell. Non-limiting examples are shown in Table 1 and Table 2 herein below.

In some embodiments, said first solution, said second solution (i.e., the core solution), or both are a polymeric solution. As used herein the phrase "polymeric solution" refers to a soluble polymer, i.e., a liquid medium containing one or more polymers, co-polymers or blends of polymers dissolved in a solvent. The polymer used by the invention can be a natural, synthetic, biocompatible and/or biodegradable polymer.

The phrase "synthetic polymer" refers to polymers that are not found in nature. Examples include, but are not limited to, aliphatic polyesters, poly(amino acids), copoly (ether-esters), polyalkylenes, oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, and combinations thereof. Further examples include: fluoropolymer polyethylene, polyethylene terephthalate, poly (tetrafluoroethylene), polycarbonate, polypropylene and poly(vinyl alcohol), and combinations thereof.

Laboratory equipment for electrospinning can include, for example, a spinneret (e.g. a syringe needle) connected to a high-voltage (5 to 50 kV) direct current power supply, a syringe pump, and a grounded collector. A solution such as a polymer solution, sol-gel, particulate suspension or melt is loaded into the syringe and this liquid is extruded from the needle tip at a constant rate (e.g. by a syringe pump).

In another embodiment, the electrospun shell of said composition comprises a polymer selected from the group consisting of poly (methylmethacrylate-co-ethylacrylate) (PMCEA), poly (e-caprolactone) (PCL), fluoropolymer, tetrafluoroethylene, sulfonated tetrafluoroethylene, polyamide, poly(siloxane), poly(silicone), poly(ethylene), poly(vinyl pyrrolidone), poly(2-hydroxy ethylmethacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(carbonate), poly(acrylo nitrile), poly(ethylene oxide), polyaniline, polyvinyl carbazole, polystyrene, poly(vinyl phenol), polyhydroxyacid, poly(caprolactone), polyanhydride, polyhydroxyalkanoate, polyurethane, polysaccharide, or a combination thereof.

In another embodiment, the electrospun core of said composition further comprises a polymer selected from the group consisting of, poly(acrylic acid), fluoropolymer, poly (vinyl acetate), polyacrylamide, poly(ethylene-co-vinyl acetate), poly(ethylene glycol), poly(methacrylic acid), polylactide polyglycolide, poly(lactide-coglycolide), polyanhydride, polyorthoester, poly(carbonate), poly(ethylene oxide), polyaniline, polyvinyl carbazole, polystyrene, poly (vinyl phenol), polyhydroxyacid, polysaccharide, or a combination thereof.

In another embodiment, said electrospun shell comprises poly (methylmethacrylate-co-ethylacrylate) (PMCEA). In another embodiment, the composition comprises 10% PMCEA in ethylacetate (EA) as a shell solution, and 10% dicyclohexylamine (DCHA) in N-Methyl-2-pyrrolidone (NMP), Triethanolamine (TEA) (1:3 by weight) as a core solution.

In another embodiment, the composition comprises 10% PMCEA in EA as a shell solution and a plurality of core solutions, wherein a first core solution comprises 10 wt. % sulfanilic acid and 10 wt. % sodium-carbonate in H2O, a second core solution comprises 25 wt. % naphthyl-ethylenediamine 2HCl in N-Methyl-2-pyrrolidone (NMP), a third core solution comprises 50 wt. % tartaric acid in H2O, and a forth core solution comprises 5 wt. % zinc dust in glycerin.

In another embodiment, the composition further comprises 20 wt. % Nylon 6,6 (polyamide,PA) in formic acid (FA): trifluoroethanol (TFE) (7:3 by weight).

In another embodiment, the composition further comprises at least one polymer compound. In one embodiment, said at least one polymeric compound provides a support (e.g., mechanical support) to said composition. In another embodiment, said at least one polymer compound is selected from the group consisting of poly (e-caprolactone) (PCL), fluoropolymer, tetrafluoroethylene, sulfonated tetrafluoroethylene, polyamide, poly(siloxane), poly(silicone), poly(ethylene), poly(vinyl pyrrolidone), poly(-hydroxy ethylmethacrylate), poly(N-vinyl pyrrolidone), poly(vinyl alcohol), poly(acrylic acid), poly(vinyl acetate), polyacrylamide, poly(ethylene-co-vinyl acetate), poly(ethylene glycol), poly(methacrylic acid), polylactide, polyglycolide, poly(lactide-coglycolide), polyanhydride, polyorthoester, poly(acrylo nitrile), poly(ethylene oxide), polyaniline, polyvinyl carbazole, poly(vinyl phenol), polyhydroxyacid, polyanhydride, polyhydroxyalkanoate, polyurethane, or a combination thereof.

In some embodiments, parameters of the electrospinning process may affect the resultant substrate (e.g. the thickness, porosity, etc.). Such parameters may include, for example, molecular weight, molecular weight distribution and architecture (branched, linear etc.) of the polymer, solution properties (viscosity, conductivity & and surface tension), electric potential, flow rate, concentration, distance between the capillary and collection screen, ambient parameters (temperature, humidity and air velocity in the chamber) and the motion and speed of the grounded collector. Accordingly, in some embodiments, the method of producing a substrate as described herein includes adjusting one or more of these parameters.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Materials and Methods

All materials were used as is: Rilsan Polyamide (PA, Arkema); Formic acid (FA) (99% LOBA Chemie); Trifluoroethanol (TFE) (99%, Sigma-Aldrich); Dicyclohexylamine (DCHA) (99%, Sigma-Aldrich); Triethanolamine (TEA) (99%, Merck); N-Methyl-2-pyrrolidone (NMP) (99.5%, Merck); Poly (methylmethacrylate-co-ethylacrylate) (PM-CEA) (Mw-101 k and 350 k gr/mol, Sigma-Aldrich); Ethylacetate (EA) (99%, Frutarom); Polyacrylonitrile (PAN) (Mw-150 k gr/mol, Sigma-Aldrich); Dimethylforamide (DMF) (99.8%, Frutarom); Sulfanilic acid (99%, Sigma-Aldrich); Sodium carbonate (99%, Sigma-Aldrich); Naphthyl-ethylenediamine-dihydrochloride (98%, Sigma-Aldrich); Zinc dust (<10 µm, 98%, Sigma-Aldrich); Glycerine oil (99%, Frutarom); Dimethylsulfoxide (DMSO) (99%, Merck); Poly(vinylidene fluoride-co-hexafluoropropylene)) (PVDF-HFP) (Mw-400 k gr/mol, Sigma-Aldrich); Tetrahydrofuran (THF) (99%, Frutarom); p-toluenesulfonic acid monohydrate (98.5%, Sigma-Aldrich); N-phenylanthranilic acid (98%, Merck); Distilled water.

Electrospinning Fibers

Figure 5:
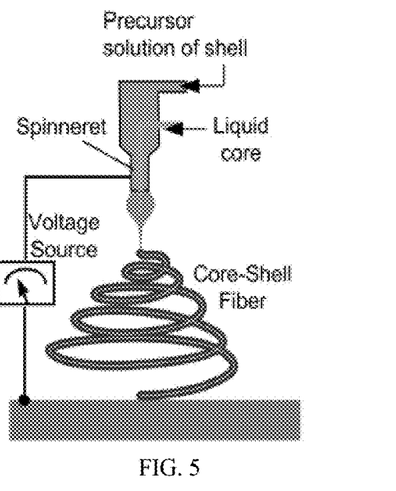
FIG. 5: Coaxial-electrospinning of liquid cored and polymer shelled nanofibers.

The co-electrospinning set up is shown in FIG. 5 and the production conditions are detailed in Table 1. A double spinneret was designed to allow for the delivery of two different liquid solutions simultaneously into a coaxial capillary, under high voltage (10 kV) between the spinneret and a grounded collector. When subjecting the polymer to a high electrostatic field (~1 kV/cm), a compound Taylor cone, composed of two coaxial cones, is formed at the tip of the spinneret. By selecting the process conditions (e.g., applied voltage, solutions feed rates) and adjusting the material properties of the polymer solutions (e.g., solution viscosities, solvent-solution miscibility, solution concentration, and solvent vapor pressure), a continuous single jet containing the two solution flows is extracted electrically out of the converging point of the Taylor cone.

Images and Spectroscopy

SEM Images were taken using a PHENOM scanning electron microscope (FEI Company), and a Zeiss ultra-plus cryogenic high resolution scanning electron microscope (cryo-HRSEM), equipped with a BAF-060 cryogenic etching chamber. Light microscope images were taken at ×115 zoom, using a SZX16 Fluorescent Binocular light microscope (Olympus), equipped with Super Depth of Focus (SDF) objective lenses, which reaches a 0.3 numerical aperture (NA) and a 900 lp/mm resolution, illuminated by an ultra-slim 40 mm LED base. Imaging of the wipe materials was taken, using a Nikon D90 DSLR camera equipped with a compatible G-type AF-S Micro-Nikkor lens having a focal length of 105 mm and a maximum aperture of f/2.8. Exposures were carried out with a lens to sample distance of ca. 40 cm. shutter speed of ⅕ sec and aperture of f/4.5. Optical absorbance scans were conducted using a GENESYS 10 UV-Vis scanning spectrophotometer (335906 Thermo Scientific equipped with a Xenon lamp). Absorbance was scanned over the range of 300-700 nm, at 1 nm/sec interval. Liquid samples were measured in quartz cuvettes and fiber samples were mounted on a designated holder. The level of detection was quantified by measuring the detection coverage (area where a color change is seen as result of the reaction) on the surface of the swab was done with Paint.Net©.

Example 1

TNT Detection and Characterization

In this work, the inventors of the present invention exemplified the concept of sampling and detecting molecules of interests using electrospun mictofibers. The exemplified molecules of interest included: a) bulk materials- of 2,4,6-trinitrotoluene (TNT), b) ammonium nitrate (AN), and c) potassium chlorate (chlorate), using the TNT-DCHA charge transfer complex formation, the Greiss 3-step reaction and NPA oxidation, respectively. As will be described hereinbelow, the detecting reagents are encapsulated in nano-scale fibers. Upon fracture of a mat of fibers during swiping, micro-gram quantities of the core reagent could be delivered onto the nanofiber surface, and reach sampled molecules of interest (e.g., explosive particles) for their subsequent detection.

Encapsulation of the reagents was carried in two methods: (1) co-axial electrospinning which enables the fabrication of a non-woven mat of nano-fiber. The shell of the fiber is made of Poly(methylmethacrylate-co-ethylacrylate) (PMCEA) characterized by a high Tg, allowing it to break down at room temperature under swiping pressure, exposing the encapsulated reagents to the explosives for visual detection. (2) Spreading the reagent to be detectable between two layers of electrospun fibers, resulting in a gel encapsulated swab. Examples of immediate visual colorimetric detection of explosives at microgram level are demonstrated.

TABLE 1 swab processing parameters of the TNT detecting swab

| Flow-rate, ml/h | Needle material/ O.D., gauge | Distance, cm | Voltage, kV | |
|---|---|---|---|---|
| 1 | Stainless steel/ 25G | 20 | 40 | Substrate: 20 wt. % Nylon 6,6 (PA) in 7:3 wt. % FA:TFE |
| 5 | Polypropylene/ 17G | 17 | 17 | Shell solution: 10 wt. % 350k PMCEA in EA |
| 5 | Stainless steel/ 21G | 17 | — | Core Solution #1: 10% DCHA in 1:3 wt. % NMP:TEA |
| 0.25 | Stainless steel/ 21G | 17 | 17 | Additional syringe: 8 wt. % PAN in DMF |

Figure 1:
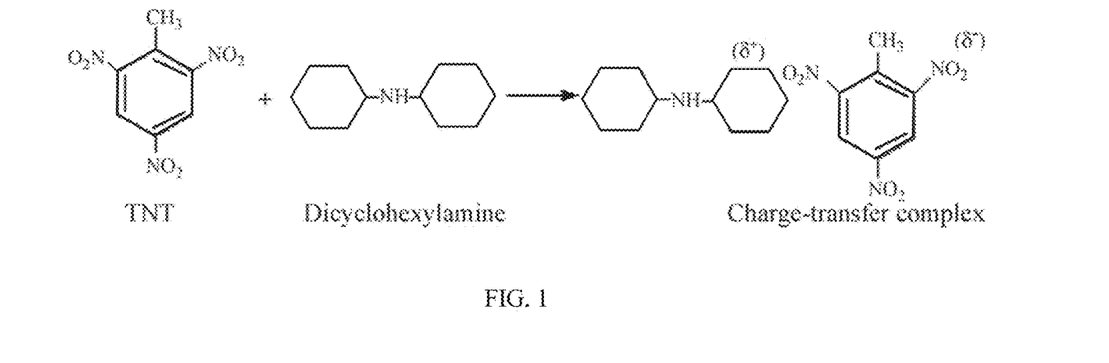
FIG. 1. 2,4,6-trinitrotoluene (TNT)—dicyclohexylamine (DCHA) charge transfer complex formation.
Figure 6:
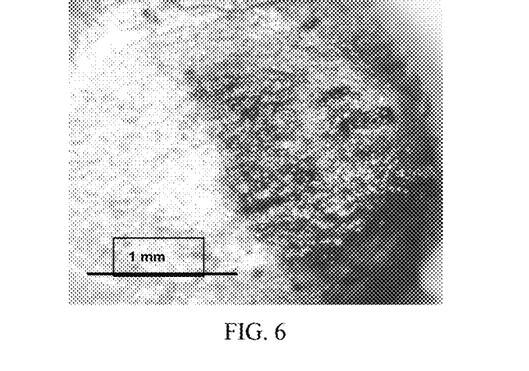
FIG. 6: Image of co-electrospun TNT detecting swab (left part of the image), and after detection of 0.05 mg TNT (right part of the image).
Figure 7A:
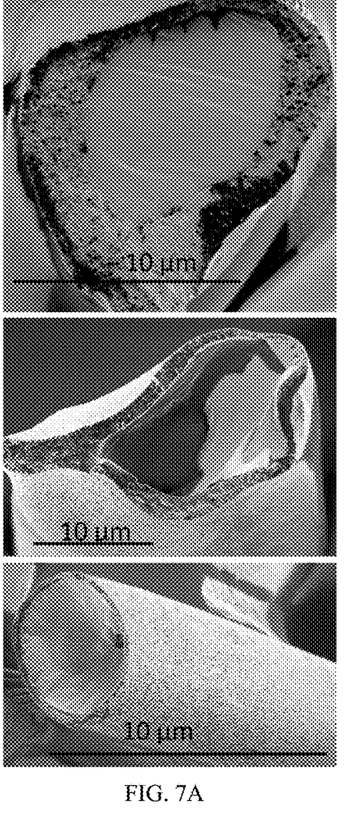
Figure 7B:
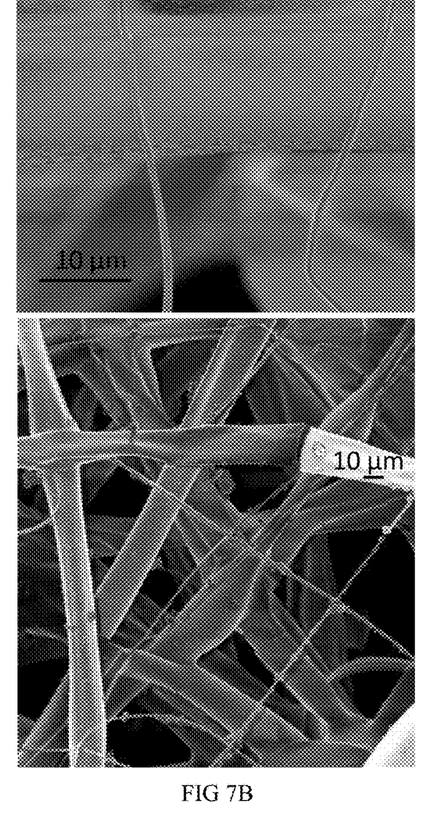
Figure 8A:
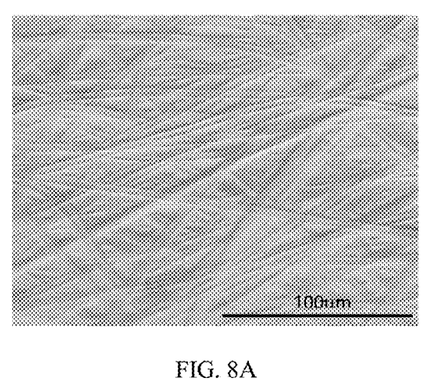
Figure 8B:
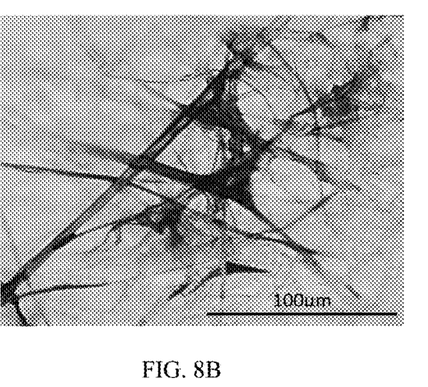
Figure 8C:
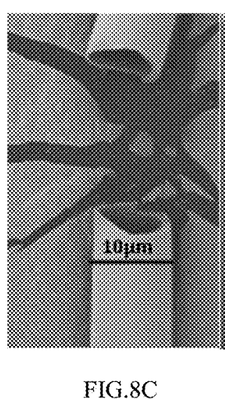
Figure 8D:
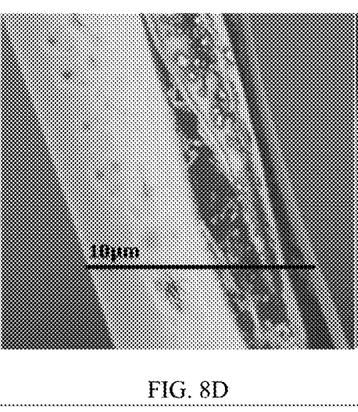
Figure 8E:
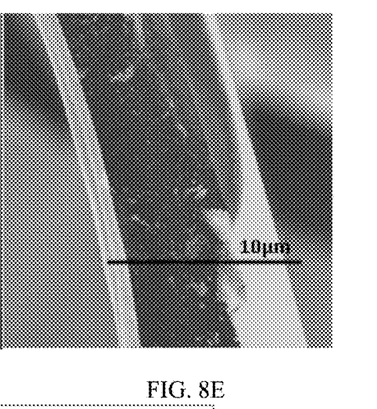

FIG. 6 shows an image of the swab immediately after swiping a quantity of 5 µg TNT from a contaminated ABS surface, which produced an immediate violet colored charge transfer complex (FIG. 1). The swab was mounted over a 5 mm diameter knob, and swiped 3 times at 0.4 kg force over 15 mm length of the contaminated ABS surface. FIG. 7 shows cryo-HR-SEM images of the reinforced core/shell-PAN network that was used for the swiping experiments.

FIG. 8 shows images of the co-electrospun mat after 0.1 mg TNT contamination and photographed within seconds, with an Olympus SZX16 Fluorescent Binocular light microscope. The high contrast between the white fibers and the colored TNT detected fibers is noticed. We can see that the color effect is displayed along the fibers, where the core was encapsulated.

Figure 9:
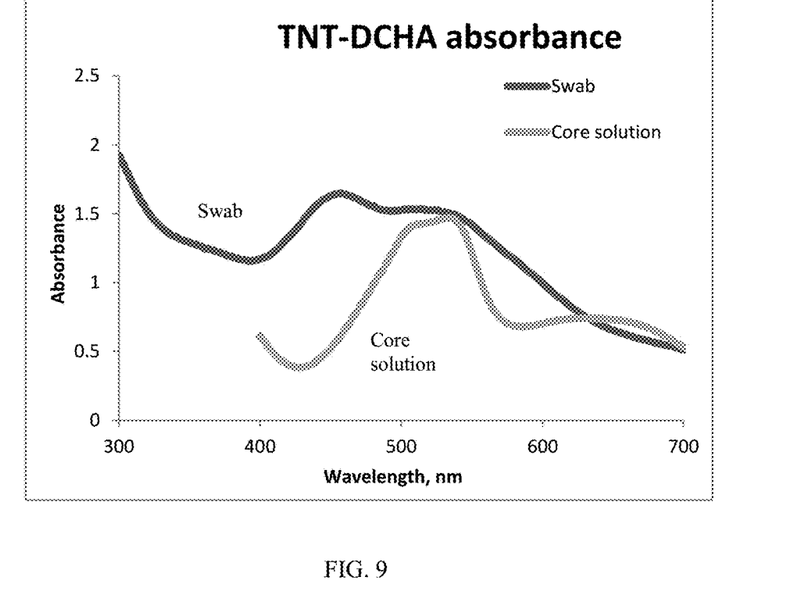
FIG. 9. Ultraviolet-visible (UV-Vis) absorbance spectrum of the DCHA-TNT complex after addition of 100 μg TNT wiped over the swab (grey line) and after being added to 3 ml of core solution (black line).

FIG. 9 shows the UV-Vis absorbance spectrum of the DCHA-TNT complex after the addition of 100 µg TNT: dispersed over a swab (grey line) and added to 3 ml of core solution (black line). As a result of the CT-complex formation, two peaks are observed at 505 and 535 nm, consisting with typical DCHA-TNT absorbance spectrum (Uzer, et al., 2004, Anal. Chim. Acta 505, 83; and Uzer, et al., 2009, Talanta 78, 772).

The TEA core solvent amine-moieties also couples to TNT to form a CT-complex. The TEA-TNT complexation result in delayed absorbance at 540 nm, due to low electron donor activity of TEA, compared to DCHA. However, the high TEA concentration in the core solution compensates for its low donor activity and increases the total absorbance in the visible region. A third absorbance peak that was obtained at 460 nm in both the swab and the core solution spectrum, is suggested to represent the moisture influence on the CT spectra in alkaline solutions, resulting in a typical absorbance of the Meisenheimer complex. (Meisenheimer, Justus Liebigs Ann. Chem. 1902, 323 (2), 205). The 460 nm peak intensity was moisture dependent, and had almost no effect when the core solution was sealed off from air moisture, however, when swab handling and measuring took place in the open lab air, moisture had a greater influence. In spite of its competition with the charge transfer color reaction, the moisture effect increased the swab's absorbance intensity in the visible region and contributed to the rapid detection of TNT.

Example 2

Nitrates Detection and Characterization

Detection of nitrates under the Greiss reaction requires a sequence of chemical reactions using zinc dust, tartaric acid, sulfanilic acid and naphthyl-ethylenediamine-dihydrochloride. Due to the limited solubility of all the four reactants of the nitrate detecting reaction in one solvent, each of the components is dissolved separately and electrospun or electrosprayed as a separate layer on the nitrate detecting swab. In this method, we were able to increase the amount of each one of the components, independently in the other ingredients. Upon swiping, the fragile shell breaks down, allowing all four components to combine and to react with nitrate contamination, and give an immediate violet detecting color on the swab's surface. The layers structures of the nitrate detecting swab are detailed in Table 2. Since the nitrates detection reaction is moisture sensitive, a drop of distilled water was drop over the swab post detection, in order to enhance the colorimetric yield.

Due to its high oxidative nature, most of the colorimetric tests for chlorates are performed in a liquid acidic medium, which may influence the swab and packaging stability once introduced to a solid product. To overcome this issue, we have used p-toluenesulfonic acid, which is a solid, non-corrosive, non-toxic acid, as a proton source for chlorate colorimetric detection.

Figure 10A:
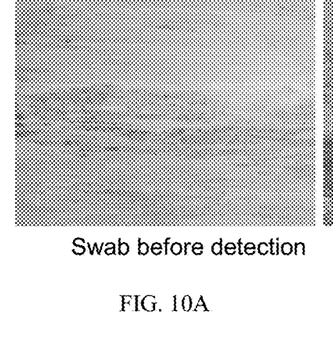
FIG. 10A. Images of the nitrate detecting swab, before (10A), and after (10B) 5 second from detection of 10 µg ammonium nitrate (AN), and after addition of one drop of water 10C).
Figure 10B:
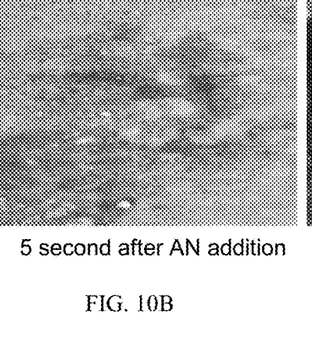
Figure 10C:
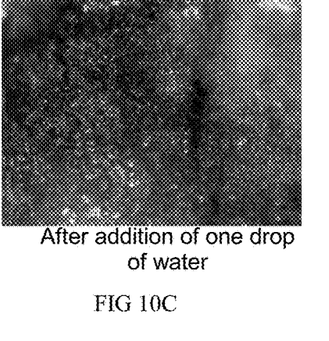

FIG. 10 (a-c) show images of the reinforced nitrates detection swab, after swiping a quantity of 10 µg ammonium nitrate from a contaminated ABS surface, and dropping one drop of distilled water over the swab, which enhanced the violet color over the swab.

TABLE 2

Nitrate detecting swab-layers structure

| Flow-rate, ml/h | Needle material/O.D., gauge | Distance, cm | Voltage, kV | |
|---|---|---|---|---|
| 1 | Stainless steel/25G | 20 | 40 | Substrate: 20 wt. % Nylon 6,6 in 7:3 wt. % FA:TFE |
| 4 | Polypropylene/17G | 17 | 17 | Shell solution: 10 wt. % 350k PMCEA in EA |
| 2 | Stainless steel/19G | 17 | — | Core Solution #1: 10 wt. % Sulfanilic acid 10 wt. % Sodium-carbonate in $H_2O$ |
| 2 | Stainless steel/21G | 17 | — | Core Solution #2: 25 wt. % Naphthyl-ethylenediamine·2HCl in NMP |
| 2 | Stainless steel/21G | 17 | — | Core Solution #3: 50 wt. % Tartaric acid in $H_2O$ |
| 0.25 | Stainless steel/21G | 17 | 17 | Additional syringe: 8 wt. % PAN in DMF |
| 2 | Stainless steel/21G | 10 | 10 | Electrospraying solution: 5 wt. % Zinc dust in Glycerin |

| Swab materials and quantity | Processing method | Layer# |
|---|---|---|
| Substrate: Nylon 6,6 - 0.3 g | Electrospinning | 1 |
| Core: sulfanilic acid - 0.5 g, sodium carbonate - 0.5 g Shell: PMCEA - 1 g | Core/shell electrospinning | 2 |
| Zinc dust - 0.2 g in Glycerin - 4 g | Electrospraying | 3 |
| Core: naphthyl-ethylenediamine-dihydrochloride - 0.5 g Shell: PMCEA - 0.4 g | Core/shell electrospinning | 4 |
| Core: tartaric acid - 2 g Shell: PMCEA - 0.8 g | Core/shell electrospinning | 5 |
| Zinc dust - 0.05 g in Glycerin - 1 g | Electrospraying | 6 |
| Polyacrylonitrile - 0.11 g | Simultaneously Electrospinning with layer 2 to 6. | 2-6 |

Figure 11:
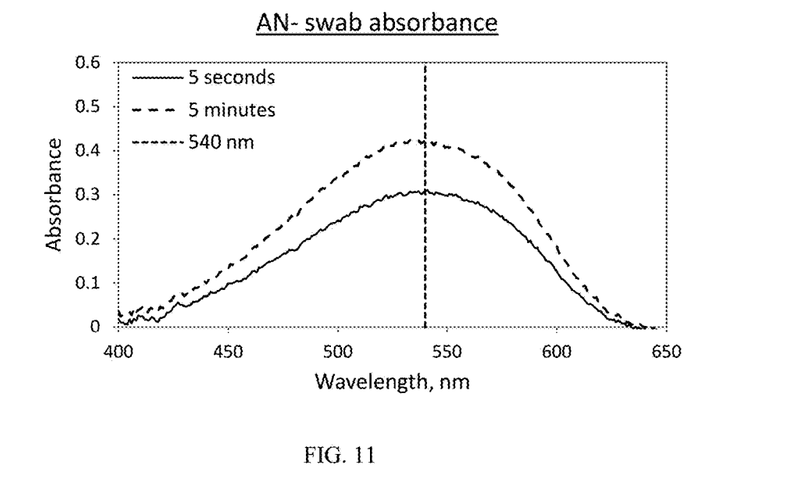
FIG. 11. UV-Vis absorbance spectra of the nitrates swab after addition of 1 mg ammonium nitrate (AN), 5 seconds (--- striped line) and 5 minutes (- continuous line) from AN addition.

FIG. 11 presents the UV-Vis absorbance spectra of the dye that was produced on the nitrates detecting swab, after detecting 10 μg AN, in 5 seconds (continuous line), and 5 minutes (dashed line) from AN addition, without the addition of water. The absorbance peak at 540 nm matches with the expected literature reported absorbance of the violet azo-dye that is produced in this reaction. The absorbance at 540 nm is increasing gradually with time (continuous and dashed lines), indicating that the reaction continues until reaching a steady state, when the entire swab is covered in the violet typical azo-dye color.

Example 3

Chlorates Detection and Characterization

Poly(vinylidene fluoride-co-hexafluoropropylene) (PVDF-HFP) nanofiber substrate showed the highest chemical resistance to p-toluenesulfonic acid during production and aging. Its hydrophobic fluorocarbon backbone resists water molecules from reaching to the hygroscopic p-toluenesulfonic acid and releasing protons. Nylon 6,6 (Polyamide,PA,) and polyacrylonitrile (PAN) however, did not withstand the high acidic conditions and their nanofibers were corroded during fabrication and aging.

TABLE 3

Chlorates detecting processing conditions

| | Voltage, kV | Distance, cm | Needle material/O.D., gauge | Flow-rate, ml/h | Time, hours |
|---|---|---|---|---|---|
| Substrate: 15 wt. % PVDF-HFP in 50:50 wt. % THF:DMF | 12 | 10 | Stainless steel/25G | 3 | 3 |

10 g of p-toluenesulfonic acid + 1 g of NPA were mixed at 40% humidity to a paste, spread over the substrate polymer fibrous layer, and covered with an additional thin PVDF-HFP fibrous layer, to give gel-encapsulated swabs.

Figure 12:
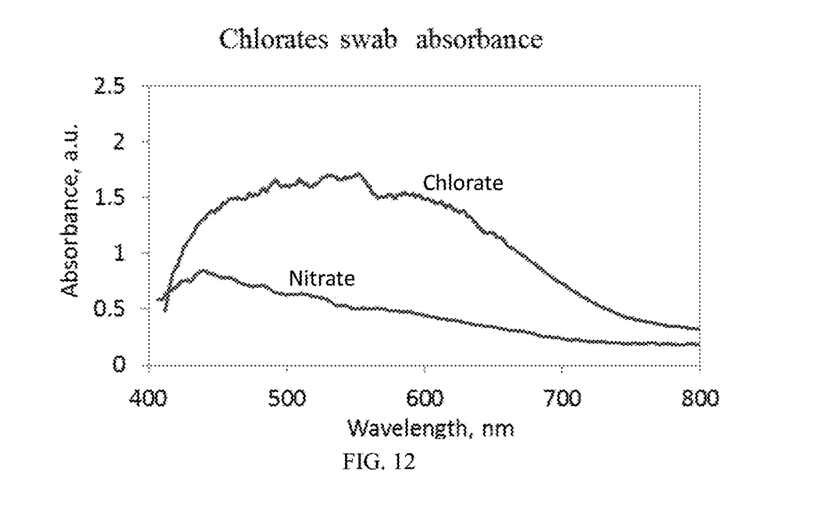
FIG. 12. UV-Vis absorbance spectra of the chlorates swab after detection of potassium chlorate (purple line) and ammonium nitrate (green line).

FIG. 20 presents the UV-vis absorbance spectra of the dye that was produced on the chlorates detecting swab, after the detection of potassium chlorate (1 second), and ammonium nitrate (5 minutes). On-swab nitrates detection resulted in a khaki green colored product ($\lambda max \approx 430$ nm), and chlorates detection resulted in a deep violet colored product ($\lambda max \approx 550$ nm). These results consist with literature, indicating on the weaker oxidation nature of the ammonium nitrate compared to the potassium chlorate, resulting in a different product.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method for the detection of an analyte on a sample, the method comprising:
    contacting the sample with a swab comprising at least one type of electrospun nanofiber and at least one colorimetric reactant, the electrospun nanofiber comprises a brittle shell and a core, said core comprises the at least one colorimetric reactant, and said brittle shell has a glass transition between 70° C. to 150° C., and is breakable under normal stress of 0.08-1 kg/cm2 at a temperature range of −55 ° C. to 60° C.,
    wherein:
        said contracting is by applying normal stress between said swab and said sample, said stress is sufficient for breaking the electrospun shell;
        a colorimetric change within the swab indicates that the sample has at least trace amounts of the analyte, thereby detecting said analyte on said surface; and
        said analyte is in a solid state, in a liquid state or both.

2. The method of claim 1, wherein said analyte is a hazardous substance.

3. The method of claim 2, wherein said hazardous substance is an explosive substance.

* * * * *